US012683017B2

(12) United States Patent
Wang et al.

(10) Patent No.: US 12,683,017 B2
(45) Date of Patent: Jul. 14, 2026

(54) SYSTEMS AND METHODS TO TRIAGE AND ASSESS SOLUTION STEPS TO EMPOWER A USER IN RESOLVING A REPORTED ISSUE

(71) Applicant: KONINKLIJKE PHILIPS N.V., Eindhoven (NL)

(72) Inventors: Lu Wang, Eindhoven (NL); Paul Soubhik, Bangalore (IN); Veena Ravi, Bangalore (IN); Qi Gao, Eindhoven (NL); Michael Günter Helle, Hamburg (DE); Sowmya Jayakumar, Bangalore (IN); Sarif Kumar Naik, Bangalore (IN); Milosh Stolikj, Eindhoven (NL); Mauro Barbieri, Eindhoven (NL); Mark Thomas Johnson, Arendonk (BE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 497 days.

(21) Appl. No.: 18/125,176

(22) Filed: Mar. 23, 2023

(65) Prior Publication Data

US 2023/0307118 A1 Sep. 28, 2023

Related U.S. Application Data

(60) Provisional application No. 63/323,678, filed on Mar. 25, 2022, provisional application No. 63/428,145, filed on Nov. 28, 2022.

(51) Int. Cl.
*G16H 40/40* (2018.01)

(52) U.S. Cl.
CPC .................................. *G16H 40/40* (2018.01)

(58) Field of Classification Search
CPC .............................. G16H 404/40; G16H 40/40
(Continued)

(56) References Cited

U.S. PATENT DOCUMENTS

2013/0132108 A1 5/2013 Solilov
2019/0236497 A1 8/2019 Santos
(Continued)

FOREIGN PATENT DOCUMENTS

WO WO-2015161062 A1 * 10/2015 ......... G07F 17/3218
WO 2021122510 A1 6/2021

OTHER PUBLICATIONS

Zhang et al. (Sep. 2019). Data-driven methods for predictive maintenance of industrial equipment: A survey. IEEE systems journal, 13(3), 2213-2227 (Year: 2019).*
(Continued)

*Primary Examiner* — Joy Chng

(57) ABSTRACT

A computer-implemented system assists resolution of service cases for medical imaging devices by retrieving device and case data, estimating likelihoods and timeframes for multiple resolution pathways, and presenting results in a user interface. Input may include images of device error messages captured by a camera; optical character recognition extracts text, and language detection and translation normalize messages for analysis. Models leverage historical repair data, technician profiles, and part replacement indicators to score pathways and forecast durations. A cost metric can combine likelihood and timeframe with service and scheduling costs to recommend actions and trigger service calls. The approach reduces downtime and improves dispatch and repair efficiency across customer and provider personnel.

12 Claims, 11 Drawing Sheets

(58) Field of Classification Search
  USPC ........................................................ 705/2–3
  See application file for complete search history.

(56)                     References Cited

U.S. PATENT DOCUMENTS

2020/0211699 A1*   7/2020   Nuthi ..................... G16H 40/40
2020/0258057 A1*   8/2020   Farahat ................. G06N 20/20
2021/0304877 A1      9/2021   Zonens
2021/0398054 A1*   12/2021   Jaggers ................. G09B 19/00

OTHER PUBLICATIONS

Keleko et al. (Mar. 10, 2022). Artificial intelligence and real-time predictive maintenance in industry 4.0: a bibliometric analysis. AI and Ethics,2(4), 553-577 (Year: 2022).*

\* cited by examiner

140

Problem:              Intermittent fatal gradient amplifier error

Related KPIs:        Number of postponed appointments

Recommended service
action owner:              Maintenance employee

Analysis result:

| | Likelihood | Cost |
|---|---|---|
| Maintenance | 4 | 8 |
| Hospital | 5 | 1 |

More details:          ...

Figure 3

SYSTEMS AND METHODS TO TRIAGE AND ASSESS SOLUTION STEPS TO EMPOWER A USER IN RESOLVING A REPORTED ISSUE

This application claims the benefit of U.S. Provisional Patent Application No. 63/323,678 filed Mar. 25, 2022 and U.S. Provisional Patent Application No. 63/428,145 filed Nov. 28, 2022. These applications are hereby incorporated by reference herein.

FIELD

The following relates generally to the medical device maintenance arts, medical imaging device maintenance arts, medical device maintenance selection arts, and related arts.

BACKGROUND

Each department in a hospital consists of multiple devices belong to different modalities which are handled by technicians belonging to that department. Most hospitals also have a central helpline team that help different departments with their device maintenance. When an issue arises in a medical device, the technicians reach out to the central helpline team who then notify the modality specific service team. Each modality comprises of dedicated service engineers (SEs) who are specialized to service devices belonging to that modality. The SE will diagnose the problem and try to resolve it remotely, if possible, else Field Service Engineers (FSEs) will be dispatched with guidance on the required parts needed for repair.

Hospital employees (i.e., biomedical engineers or "biomeds") are responsible for maximizing the efficiency of the systems at the facility to deliver high quality patient care. In some cases, the bio-meds are the first contact point to investigate issues with medical equipment. Hospitals are on a transformation wave from fee-for-service to value-based care, thus cost and value are important indicators for bio-meds.

Over the years, competence of bio-meds of hospitals have changed too. They are no longer only focused on medical device installation and maintenance but also have been integrating tighter connections with medical software.

However, bio-meds have limited knowledge and experience to diagnose the root cause of a problem with a medical device. When a bio-med is unable to resolve a problem, a service engineer from the manufacturer or a third-party servicing provider may be called in. However, this entails a cost to the hospital, and the decision of whether a bio-med should handle a problem personally or refer it to a service engineer should take cost and value for the hospital into account. For instance, if a repair could be done by a bio-med but doing so would lead to rescheduling treatments for high grade cancer patients, then it is better to call for support from the manufacturer or a more specialized third-party vendor. In another case, a repair that could be easily performed by a bio-med causing rescheduling a few mild patient cases, could save a visit from the manufacturer and third-party vendor engineer, as well as reducing the overall cost.

In addition, service and maintenance is an important aspect of a vendor's medical equipment business. Timely service and resolution to a reported problem is one of the key factors contributing to customer satisfaction. Some vendors have a dedicated department for providing and managing the service and maintenance activities including Remote Service Engineers and Field Service Engineers (FSE) providing servicing across the globe. Whenever the customer reports an issue an RSE is appointed to attend to the issue and remotely diagnose it and if possible, fix it as well. If the RSE is unable to fix the issue, then an FSE is assigned to visit the site and fix the problem. Often, due to limited resource constrains resolution to reported problems get delayed. There are also customer feedbacks where they complain the SE taking longer than estimated time provided.

In a current workflow, a solution to a reported issue contains different steps that needs to be performed by FSEs and it is often seen that certain steps are easy/straight forward (but time consuming & important) which does not need special technical skills and can be performed by a non-technical person such as the user.

The following discloses certain improvements to overcome these problems and others.

SUMMARY

In one aspect, a non-transitory computer readable medium stores data related to medical imaging devices, and instructions readable and executable by at least one electronic processor to retrieve, based on a query received for a current service case, data related to a current medical imaging device for which the current service case to be performed; retrieve at least one service case resolution workflow comprising tasks for the current service case; identify, from the retrieved data and the at least one service case resolution workflow, (i) a first subset of the tasks of the at least one service case resolution workflow to be performed by a customer of the current medical imaging device, and (ii) a second subset of the tasks of the at least one service case resolution workflow to be performed by a service engineer; provide, on a display device of an electronic processing device, a user interface (UI) showing (i) the identified first subset of the tasks of the at least one service case resolution workflow to be performed by the customer and (ii) the identified second subset of the tasks of the at least one service case resolution workflow to be performed by the service engineer.

In another aspect, a non-transitory computer readable medium stores data related to medical imaging devices; and instructions readable and executable by at least one electronic processor to retrieve, based on a query received for a current service case, data related to a current medical imaging device for which the current service case to be performed; generate, from the retrieved data and for each of a plurality of available service case resolution pathways, (i) a resolution likelihood score indicative of a likelihood of the resolution pathway resolving the current service case, and (ii) a timeframe for the resolution pathway to resolve the current service case; and provide, on a display device of an electronic processing device, a user interface (UI) displaying the generated resolution likelihood score and the generated timeframe for the resolution pathways.

In another aspect, a method for determining a resolution pathway for the medical device while undergoing servicing includes generating, from data related to a current medical imaging device for which the current service case to be performed, and for each of a plurality of available service case resolution pathways, (i) a resolution likelihood score indicative of a likelihood of the resolution pathway resolving the current service case, and (ii) a timeframe for the resolution pathway to resolve the current service case; providing, on a display device of an electronic processing device, a UI the generated resolution likelihood score and the generated timeframe for the resolution pathways; and receiving a selection of an indication of a selection of the resolution pathway to resolve the current service case.

In another aspect, a servicing support system includes a database storing data related to medical imaging devices; and at least one electronic processor programmed to retrieve, based on a query received for a current service case, data related to a current medical imaging device for which the current service case to be performed; generate, from the retrieved data and for each of a plurality of available service case resolution pathways, (i) a resolution likelihood score indicative of a likelihood of the resolution pathway resolving the current service case, (ii) a timeframe for the resolution pathway to resolve the current service case, and (iii) a cost of resolution for the current service case; and provide, on a display device of an electronic processing device, a UI displaying the generated resolution likelihood score, the generated timeframe for the resolution pathways, and then cost of resolution.

One advantage resides in providing assistance to hospital employees to select a pathway to resolve service cases for medical devices.

Another advantage resides in facilitating decisions by hospital employees to either resolve a service case themselves or call a manufacturer or maintenance employee.

Another advantage resides in reducing repair costs for a medical facility.

Another advantage resides in reducing downtimes and rescheduled treatments for medical devices at a medical facility.

Another advantage resides in providing solution to medical device maintenance issues that do not require the assistance of FSE's but can be resolved by the hospital technician themselves by providing point wise directions by mining similar historical incidents.

Another advantage resides in providing instant solution to medical device maintenance issues, thereby increasing the customer support and satisfaction.

Another advantage resides in reducing imaging device downtime at the customer site along with an overall time to resolve a medical device maintenance issue.

Another advantage resides in identifying non-trivial medical device maintenance issues that do not require FSE's guidance or support, thereby considerably reducing the FSE's workload.

Another advantage resides in providing translation services for medical maintenance device issues.

Another advantage resides in improving a present workflow of resolving a reported problem by service engineers, so that the solution to a problem can be performed on time even with limited resource constraints.

Another advantage resides in optimizing a required time to solve a problem of FSE and also help the FSE concentrate on the actual critical steps without wasting time in time consuming trivial steps.

Another advantage resides in reducing delays in resolutions of reported problems due to resource constraints.

Another advantage resides in empowering a user of a medical device to assist in solving a problem with the medical device.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

FIG. 3 shows a user interface generated by the system of FIG. 1.

DETAILED DESCRIPTION

Figure 1:
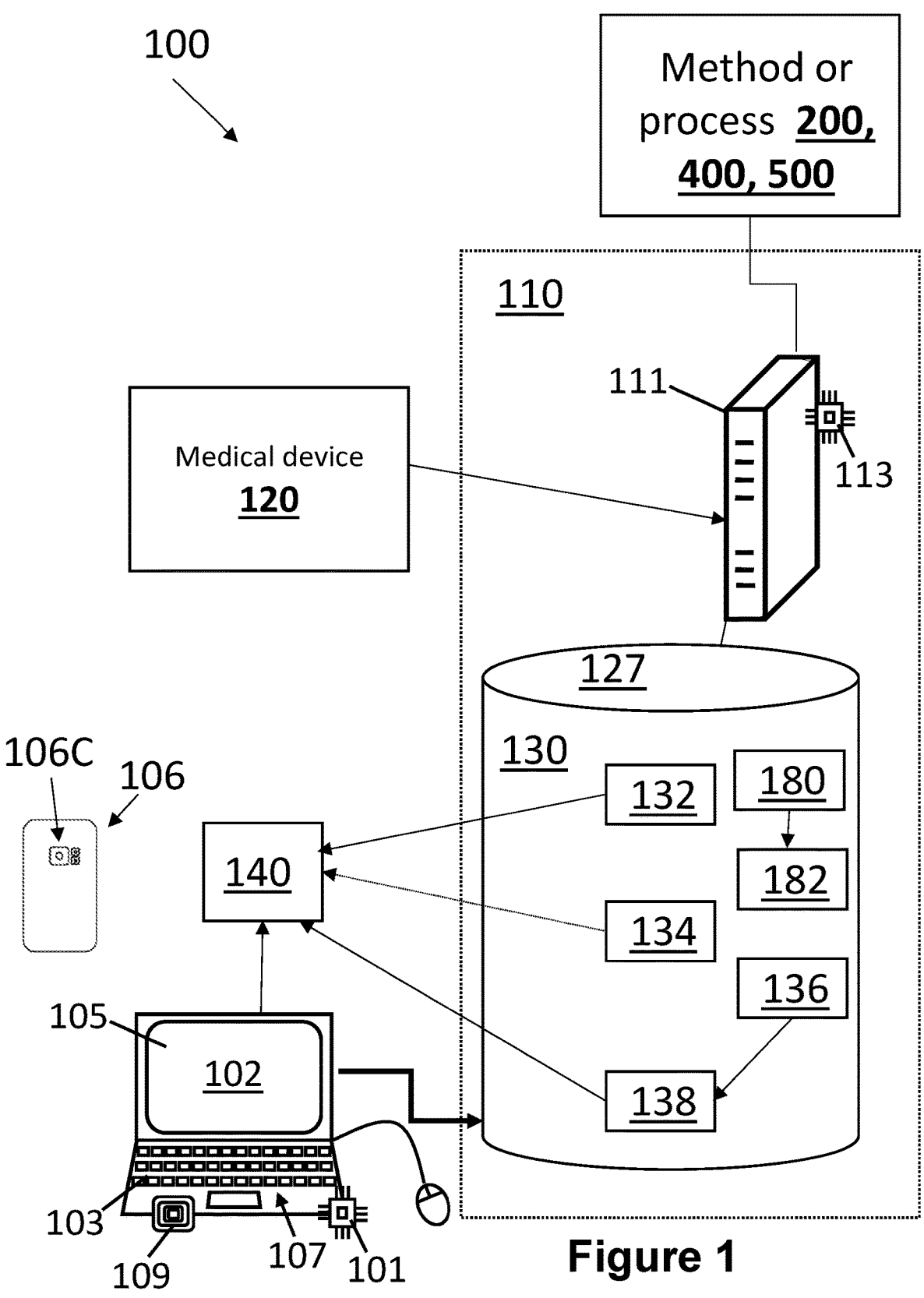
FIG. 1 diagrammatically illustrates an illustrative system for servicing medical devices in accordance with the present disclosure.

When a problem arises with a medical imaging device and is initially triaged, a decision is then made as to whether the problem should be repaired "in-house" by hospital staff, or by the equipment vendor or a third-party maintenance provider (collectively referred to herein as "maintenance service provider"). Regarding the former option, hospitals and other medical institutions may have staff personnel qualified to perform limited maintenance on a medical imaging device. The title and background of such personnel varies amongst institutions. In some cases, a biomedical engineer (bio-med) may serve in this role. The bio-med typically has training such as biological training, mechanical or electrical engineering training, and may in some cases be a medical doctor (M.D.) or an imaging technician who was promoted to the bio-med position. In smaller hospitals, the in-house maintenance person may be an information technology (IT) staffer with some training on at least the electronic systems of the medical imaging device.

As will be appreciated, the in-house maintenance person will have limited capabilities in the area of medical imaging device maintenance. However, where a problem can be resolved in-house this can be more efficient and may reduce downtime. For example, if the problem renders the imaging system unusable for some or all imaging tasks, then the delay in scheduling a service call from the maintenance service provider may be avoided. On the other hand, if a bio-med or other hospital staffer attempts to solve the problem in-house and fails, this introduces delay and potential additional imaging device downtime that could have been avoided had a maintenance service provider been immediately called.

The following discloses a system for advising whether a problem should be resolved in house or by the maintenance service provider (or possibly some other resolution pathway, such as a "self-help" guided wizard that could be used by the imaging technician who reported the problem). To this end, the system includes an information extraction component, a likelihood and timeframe assessment component, an analysis component, and a user interface.

The information extraction component collects relevant data from various sources, such as the service record, scheduling information and key performance indicator (KPI) information (for assessing the impact of downtime). The information sources may be within the hospital IT network, retrieved from the maintenance service provider, from a software company, and/or a combination thereof. Assessment of the impact of downtime may optionally account for factors such as the availability (or lack thereof) of other medical imaging devices capable of performing imaging examinations scheduled to be performed by the medical imaging device that is the subject of the current service case, and/or the extent to which the medical imaging device is used for emergency imaging tasks.

The likelihood and timeframe assessment component consumes this information and computes two estimates for each actor (in-house servicing or external maintenance service provider): (1) the actor's likelihood of resolving the problem; and (2) a timeframe for the actor to resolve the problem. The likelihood of resolution may be based on information such as number of historical cases resolved in-house versus resolved by the maintenance service provider, and historical effectiveness of the actor's resolution (e.g., quantified by fraction of historical cases resolved by the actor which recurred within a designated subsequent time interval), and more particularly in some nonlimiting illustrative embodiments on the likelihood that resolution may entail a non-customer-serviceable part replacement. For the likelihood and timeframe assessment of the in-house actor, a further factor may be the background of the in-house actor—for example, if the in-house actor is an IT person, then the likelihood of that person successfully resolving a hardware problem may be low or even zero, whereas a bio-med with a mechanical engineering background may have a higher likelihood of success. The background of the in-house actor may also include training records of the in-house records if such are available in electronic format. For example, some medical imaging device vendors may provide training programs and/or provide certification based on completed online or in-person training, and these records may then be available electronically for use in the assessment. For the timeframe assessment, suitable inputs include historical case resolution times, for example.

The analysis component consumes the likelihood and timeframe estimates and applies a cost metric to assess an equivalent cost of resolution by each actor. This component may also consume KPIs to assess costs, possibly including both direct monetary costs (such as the service call charge) and indirect costs such as rescheduled appointments determined based on the timeframe and the schedule information. The user interface provides the results, which in the illustrative example include the likelihood and cost information.

In a variant embodiment, the analysis component could be omitted, and the likelihood and timeframe estimates could serve as the output.

In a customer-facing embodiment, the user interface is used by an in-house hospital administrator to assist in deciding whether to attempt to resolve the problem in-house or call the maintenance service provider. In a provider-facing embodiment, the user interface is used by a remote service engineer (RSE) handing a customer call to assist in deciding whether to recommend the customer resolve the problem directly or whether to send a field service engineer (FSE). Operation of the system is substantially similar in both cases, although the choice of KPIs may differ.

In some embodiments, the disclosed system employs a cellphone camera or the like to acquire an image of a displayed error message. The image is processed by optical character recognition (OCR) to extract the text (letters in a language like English, or characters in a language like Chinese) and the language is automatically detected based on the extracted text. If necessary, the text is automatically translated using natural language processing (NLP) translation into the common language used by the system (i.e., English as used herein). Additionally, the user may optionally elect to type (or dictated by audio transcription) additional comments or information which are similarly processed if needed to translate to the common language.

The resulting information in the common language is then input to a database (e.g., a relational database or the like) which outputs a grade and a timeframe for solving the problem for each pathway. This involves two pathways: Grade 1—solve in-house by a biomed; or Grade 2—call to the maintenance service provider.

If the recommended solution is to solve in-house by the biomed (Grade 1) then an automated decision tree or wizard or the like may be provided to guide the biomed through the process of solving the problem. If the biomed is unable to resolve the problem within a reasonable time frame (e.g., chosen based on the expected solution timeframe output by the database) then the user may be asked if he or she wants to place a maintenance service call.

The following uses a binary grading system. However, the grading system could be more elaborate, e.g., including additional categories (FSE/biomed/wizard, for example) and/or a continuous grading system providing information equivalent to a likelihood of solution. (For example, if a computed continuous grade is 0.9 this may be interpreted as indicating it is very likely the biomed can resolve the problem in-house; whereas a grade of 1.3 might be interpreted as a recommendation to solve the problem in-house by the biomed but with a lower likelihood of success than would be inferred from a score of 0.9.

In another aspect disclosed herein, the proposed systems and methods include analyzing the resolution workflow to identify straightforward steps that can be performed by the customer and assigning those steps to the customer, while the remaining more complex steps are performed by an FSE. This provides advantages including faster FSE visits and allowing the FSE to concentrate on the more complex steps of resolving the service case. This approach can also provide empowerment to the customer who can thereby positively contribute to resolving the issue, and in some implementations can reduce the resolution cost for the customer.

The illustrative solution involves an offline phase, and a case-specific phase. In the offline phase, various solution workflows provided in a service manual, or the like are analyzed. For each workflow, an ordered sequence of solution steps is identified based on the numbered or bullet items contained in the service manual, or extracted from a workflow flowchart provided in the service manual. The text of each step is analyzed by natural language processing (NLP) to characterize the text content of each step by keywords, named entities, N-grams, topic analysis, and/or so forth. This input (the ordered sequence of steps and the features representing each step) serve as input to a machine learning (ML) model that classifies each step as to complexity and whether it depends on an earlier step. The ML model can be trained on a subset of workflows that are annotated with the complexity/dependency information, and thereafter the ML model can be applied to other (unannotated) workflows. This completes the offline phase, whose output is the sequence of steps labeled with complexity/dependency classifications.

In the per-case phase, a new case comes in. The workflow for that case (or, in a variant embodiment, multiple possible workflows) is identified, and the sequence of steps labeled with complexity/dependency classifications is retrieved for that workflow. A further input is the customer skill level.

With this information, customer-assigned steps are identified that are within the customer skill level (i.e. whose complexity is low enough for the customer to handle) and that do not depend on an earlier step that cannot be performed by the customer. Additionally, a step is added after the final customer-assigned step which instructs the FSE to check the customer's work. The customer-assigned tasks are then assigned to the customer, and the service case is assigned to an FSE who is scheduled to perform the servicing. The FSE visit should be scheduled so that the customer can perform the customer-assigned steps ahead of the FSE visit.

With reference to FIG. 1, an illustrative servicing support system 100 for supporting a service engineer in servicing an electronic device 120 (e.g., a medical imaging device—also referred to as a medical device, an imaging device, imaging scanner, and variants thereof) is diagrammatically shown. By way of some non-limiting illustrative examples, the medical imaging device under service may be a magnetic resonance imaging (MRI) scanner, a computed tomography (CT) scanner, a positron emission tomography (PET) scanner, a gamma camera for performing single photon emission computed tomography (SPECT), an interventional radiology (IR) device, or so forth. (More generally, the disclosed approach can be applied in conjunction with any type of computerized device that automatically generates log data, e.g., the approach could be applied to a commercial airliner, radiation therapy device, or so forth).

As shown in FIG. 1, the servicing support system 100 includes, or is accessible by, a service device 102 that may for example be a workstation or electronic processing device used by a user (e.g., a service engineer (SE), such as a remote SE (RSE) or a field SE (FSE)). The service device 102 may for example be a portable device such as a notebook computer that is carried or accessed by an RSE. The service device 102 can be a desktop computer or a personal device, such as a mobile computer system such as a laptop or smart device. In other embodiments, the service device 102 may be an imaging system controller or computer integral with or operatively connected with the imaging device undergoing service (e.g., at a medical facility). As another example, the service device 102 may be a portable computer (e.g., notebook computer, tablet computer, or so forth). In another example, the service device 102 may be the controller computer of the imaging device under service, or a computer based at the hospital. In other embodiments, the service device may be a mobile device such as a cellular telephone (cellphone) or tablet computer.

The service device 102 includes a display device 105 via which the user may enter a query summarizing a problem with the medical imaging device 120. For example, the service device 102 may provide a support ticket entry system for entering the query summarizing the problem in the form of a support ticket. In another embodiment, the servicing support system receives the query as an image, received from a digital camera or an electronic device such as an illustrative cellular telephone (cellphone) 106 that includes a digital camera 106C (note, the cellphone 106 is shown in backside view in FIG. 1 to illustrate the backside camera 106C which is typically the high-resolution camera compared with the frontside camera of a typical cellphone), of an error message generated by the medical imaging device 120. In this latter case, the query image can be processed by optical character recognition (OCR) to extract the imaged error message indicating the problem with the medical device. The digital image can be received by the service device 102 from the cellphone 106 via a wired USB cable or other wired connection (not shown), or via Bluetooth™, Wi-Fi, or another wireless data transmission protocol. In some embodiments, the service device 102 itself may be the electronic device with the digital camera that acquires the image of the error message. For example, the illustrative computer 102 may be a notebook computer with a built-in digital camera (e.g., webcam) that can be used for this purpose; or, if the service device 102 is a cellphone, then the digital camera of the cellphone can be used to acquire the image. Optionally, the servicing support system may provide a user interface (UI) via which additional text can be submitted with the image, for example as a textual annotation of the image of the error message indicating potentially useful diagnostic information such as the circumstances around the error message (e.g., the type of imaging examination being performed, the scan being run, and/or so forth). The service device 102 allows the service engineer to interact with the ticketing or other servicing support system via at least one user input device 103 such as a mouse, keyboard, or touchscreen. The service device 102 further includes an electronic processer 101 and non-transitory storage medium 107 (internal components which are diagrammatically indicated in FIG. 1). The non-transitory storage medium 107 stores instructions which are readable and executable by the electronic processor 101 for interfacing with the servicing support system 100. The service device 102 also includes a communication interface 109 to communicate with a backend server or processing device 111, which typically implements the computational aspects of the servicing support system 100 (e.g., the server 111 has the processing power for implementing computationally complex aspects of the servicing support system 100). Such communication interfaces 109 include, for example, a wired and/or wireless Ethernet interface or a wireless Wi-Fi or 4G/5G interface or the like for connection to the Internet and/or an intranet. Some aspects of the servicing support system 100 may also be implemented by cloud processing or other remote processing (that is, the server computer 111 may be embodied as a cloud-based computing resource comprising a plurality of interconnected servers).

In illustrative FIG. 1, the servicing support system further includes a backend 110 (e.g., implemented and/or owned by the imaging device vendor or leased by the vendor from a cloud computing service provider, or implemented and/or owned by the hospital). The backend 110 receives the query (e.g., the service request ticket or the image of the error message, in two illustrative examples) and may also receive other relevant information such as log data (e.g., a machine log automatically generated by the medical imaging device 120, a service log for the medical imaging device 120, and/or so forth) or additional text entered along with the image of the error message. The backend server 111 is equipped with an electronic processor 113 (diagrammatically indicated internal component), and with a non-transitory storage medium 127 (internal components which are diagrammatically indicated in FIG. 1). While a single server computer is shown, it will be appreciated that the backend 110 may more generally be implemented on a single server computer, or a server cluster, or a cloud computing resource comprising ad hoc-interconnected server computers, or so forth.

The non-transitory computer readable medium 127 stores a database 130 including data related to one or more medical device(s) 120. The data related to the medical imaging device(s) 120 includes one or more of a service record of the current medical device (i.e., the medical imaging device 120), scheduling information for the current medical imaging device, and key performance indicator (KPI) information related to an impact of downtime of the current medical imaging device. The database 130 storing the data related to the medical imaging devices 120 is operable by the customer of the current medical imaging device 120, or a maintenance provider capable of providing service for the current medical imaging device 120.

The non-transitory storage medium 127 also stores instructions executable by the electronic processor 113 of the backend server 111 to perform a method 200 of determining a resolution pathway for the medical device 120 while undergoing servicing.

Figure 2:
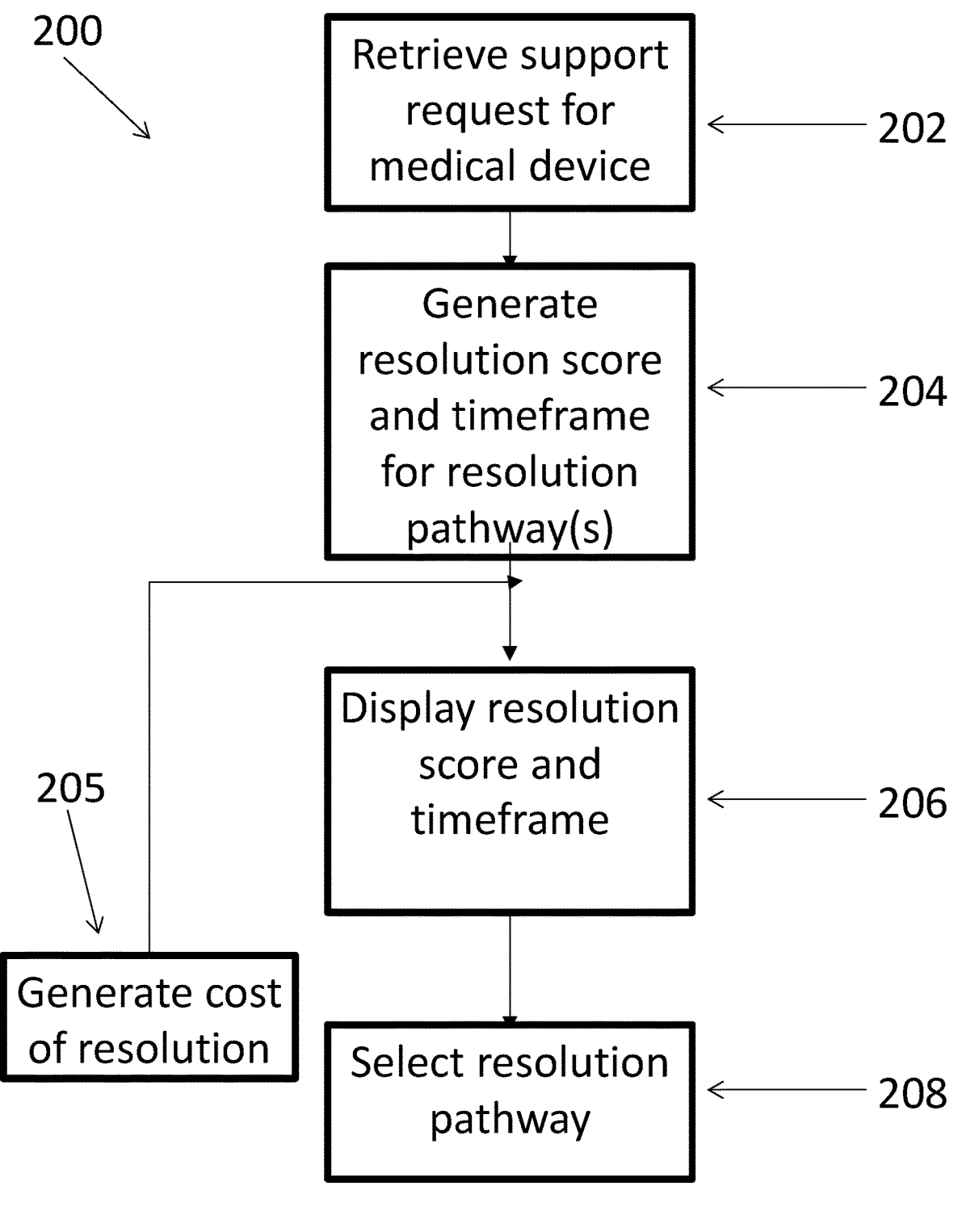
FIG. 2 shows exemplary flow chart operations of the system of FIG. 1.

With continuing reference to FIG. 1 and further reference to FIG. 2, an illustrative embodiment of the method 200 executable by the electronic processor 113 of the backend server 111 is diagrammatically shown as a flowchart. In some examples, the method 200 may be performed at least in part by cloud processing.

At an operation 202, a support request (i.e., query) for the medical device 120 is received, and data related to the medical device 120 is retrieved from the database 130. The support request could, for example, be in the form of a support request ticket filled out by an imaging technician who encounters a problem while using the illustrative medical imaging device 120. In another approach, the imaging technician makes the support request orally (e.g., via telephone) and the bio-med or another intake person enters the orally received support request into the system. In another approach, the query received at the operation 202 could be a received image of an error message displayed by the medical imaging device 120. (In this context, the medical imaging device may be understood as including any component of the medical imaging device 120 that is configured to display an error message relating to the medical imaging device, such as the electronic controller of the medical imaging device 120. Furthermore, the medical imaging device 120 in this context may include a display of ancillary equipment used with the medical imaging device in performing medical imaging, such as for example a display of a contrast agent injector used with an MRI or CT scanner to perform contrast agent-enhanced MRI or CT imaging.

At an operation 204, a resolution likelihood score 132 indicative of a likelihood of a resolution pathway resolving the current service case, and a timeframe 134 for the resolution pathway to resolve the current service case are generated from the retrieved data, As used herein, the term "resolution pathway" (and variants thereof) refer to a maintenance provider employee who is a service engineer (SE) of a manufacturer or vendor of the medical device 120, or a biomedical engineer ("bio-med") who is a customer employee of a medical facility where the medical device 120 is located. The resolution pathway in some embodiments can also be another type of resolution pathway such as a self-help "wizard" software program implemented on the service device 120 to guide a user through the method 200.

In the illustrative embodiments, the resolution pathways that are analyzed in operation 204 include a customer employee and a maintenance provider employee. The customer employee resolution pathway is a customer employee of a medical facility where the medical device 120 is located. For this resolution pathway, the generating operation 204 includes generating the resolution likelihood score based on a historical effectiveness 132 of the customer employee in resolving historical service cases within a predetermined timeframe for the medical device 120. In one example the resolution likelihood score 132 is generated further based on a background of the customer employee. Quantitative metrics of the background of the customer employee could include, by way of nonlimiting illustrative example: employee professional title (e.g., a customer employee with an IT title may have a low likelihood of resolving a current service case requiring actions pertaining to system hardware but may have a higher likelihood of resolving a current service case relating to a software issue); training records (e.g., if the customer employee has completed training and/or certification programs relating to the current service case then this enhances likelihood the customer employee can successfully resolve the current service case); seniority (a more senior customer employee may in general be expected to be more likely to resolve the current service case compared with a recent hire); and/or so forth.

The resolution likelihood score for the customer employee may further include a metric relating to whether resolution of the current service case is likely to involve replacement of a part, and if so whether that part replacement is considered a customer-serviceable operation. For example, if there is a substantial likelihood that a part replacement will be required (either immediately to resolve the current service case or in the near future if the issue portends a likely-imminent part failure) and that part replacement is not a customer-serviceable operation, then this metric may reduce the timeframe and/or likelihood of success scores. This metric can be determined, for example, using a suitably trained machine learning (ML) model that is trained on historical service cases to predict likelihood of a part replacement based on occurrences thereof in similar historical service cases, along with a database of non-customer-serviceable parts.

The maintenance provider employee resolution pathway is a maintenance provider employee of a vendor of the medical device 120. For this resolution pathway, the generating operation 204 includes generating the resolution likelihood score 132 based on a historical effectiveness of the maintenance provider employee in resolving historical service cases within a predetermined timeframe for the medical device 120. These likelihoods may again in some nonlimiting illustrative embodiments be based in part on metric relating to whether resolution of the current service case is likely to involve replacement of a part, and if so whether that part replacement is considered a customer-serviceable operation. Here though, a high value for the metric indicating a likely non-customer-serviceable part replacement suitably increases the likelihood of resolution score 132 for the maintenance provider employee resolution pathway.

In an optional operation 205, a predetermined cost metric 136 (stored in the non-transitory computer readable medium 127) is applied to the generated resolution likelihood score 132 and the generated timeframe 134 to determine a cost of resolution 138 for the current service case. The cost of resolution 138 can be determined by determining a cost of a service call for the current service case and/or costs related to scheduling data related to the current medical imaging device 120. For example, the cost of resolution 138 may account the impact of downtime of the medical device 120 as measured by one or more KPIs. Assessment of the impact of downtime may optionally include a KPI measuring availability (or lack thereof) of other medical imaging devices capable of performing imaging examinations scheduled to be performed by the medical imaging device that is the subject of the current service case. For example, if the hospital has six MRI scanners of the same or similar capability, then the impact of downtime for one of those six MRI scanners is likely to be lower than would be the case if the hospital had only a single MRI scanner. This KPI could for example be the number of similar medical imaging devices (or a function thereof; where for example a second imaging device might be deemed similar to a first imaging device that is subject of the current service call if the second imaging device can perform at least a threshold fraction of historical and/or currently scheduled imaging examinations of the first imaging device). The assessment of downtime impact may also optionally include a KPI measuring the extent to which the medical imaging device is used for emergency imaging tasks. For example, if the hospital has six MRI scanners but the one that is subject of the current service case is physically located in or near the emergency department and commonly used for imaging emergency cases, then the impact of downtime for that MRI scanner may be higher than would be the case for an MRI scanner that is located far away from the emergency department, for example in a surgical rehabilitation department. This KPI might, for example, be quantified as the fraction of historical and/or currently scheduled imaging examinations of the current medical imaging device for which the current service case to be performed which are emergency imaging exams.

At an operation 206, a user interface (UI) 140 is provided on the display device 105 of the service device 102, and the resolution likelihood score 132 and the timeframe 134 are displayed on the UI 140. When generated, the cost of resolution 138 can also be displayed on the UI 140.

At an operation 208, the resolution pathway is selected. In one embodiment, a user input is received, via the user input device 103, from a user of the service device 102 (e.g., a customer of the medical device 120 who initiated the query for the current service case, which can be a remote SE (RSE)). The user input is indicative of a selection of the resolution pathway (e.g., the customer employee or the maintenance employee) to resolve the current service case.

In another embodiment, the resolution likelihood score 132 and the timeframe 134 are generated for each possible resolution pathway (e.g., the customer employee, the maintenance employee, and so forth). The resolution pathway having the highest resolution likelihood score 132 can be selected (e.g., by the RSE) to resolve the current service case. A service call can then be scheduled with the selected resolution pathway.

EXAMPLES

The following describes the system 100 and the method 200 in more detail. The system 100 is configured to extract information stored in the database 130, including the historic service record of the medical device 120, hospital's KPI's and scheduling software (at least in the radiology department), as well as connected to vendor's historic service record on similar medical devices 120. The reported date could be served as a filter to extract scheduling information. Additionally, the problem, error code and symptoms of the medical device 120 can be used to filter relevant information too.

The system 100 is then configured to identify the most relevant technical documents and historical service records for similar problems in other medical devices of the same type. The complexity (or difficulty) of the service action can be specified within the technical documentation, or it can be estimated dynamically, by a machine learning (ML) model implemented in the backend server 111. The ML model can use the textual description of the service action as input for the assessment, or, in addition, can use historical service records from medical devices of the same type.

The system 100 then summarizes a solution profile from similar medical devices with the same problem. This solution profile contains at least the number of solutions that were solved by each action owner, the duration it took, as well as the actual performed steps and their complexity level.

Predefined rules can be used to estimate the likelihood score 132 (low or high) the issue to be resolved by different service providers, for instance, if the similar cases were mostly escalated, it suggests a low likelihood for a bio-med to fix it; if a similar case was resolved by the bio-med and the complexity analysis from the technical documents suggested low, then the likelihood for a bio-med to solve the case is high. Alternatively, one can use learnable functions to compute a likelihood equation according to:

$$L(S)=\text{Function}(C,E,R)$$

L: likelihood
S: service provider (e.g., bio-med)
C: complexity analysis from technical documents
E: number of escalated cases of the similar problem in the history
R: reoccurrence of the problem on this medical device In addition to the likelihood score 132, the timeframe 134 predicts the time that will be required to resolve the problem can be generated. The timeframe 134 can be represented as a single value (e.g., average resolution time of similar problems in the past), or a distribution according to:

$$T(S)=\text{Function}(C,R)$$

T: time required to resolve the problem
S: service provider (e.g., bio-med)
C: complexity analysis from technical documents
R: repair time of historical service records, for the same medical device type, performed by the same type of service provider(s)

The system 100 is then configured to use the hospital KPI's or measures, together with the likelihood score 132 and the timeframe 134 to estimate the cost of resolution 138 to the hospital. Alternatively, if replacing hospital's KPI to a vendor's KPI, it can estimate the cost of resolution 138 for the vendor.

One of these KPI's can be an impact of postponed schedules, in which the scheduling informatics of the planned appointments within the predicted service time can be extracted. The impact of estimated postponed appointments is a weighted number suggesting the impact from postponing patients' appointments if this medical device could not function in the estimated period of time. The method can also extract information from other medical devices and estimate available timeslots. Then the number of estimated postponed schedules can be reduced. In more advanced situation, clinical evaluation (e.g., TNM) of a patient could be used to balance the importance of certain appointments, according to:

$$ImP=\text{Sum}(Psi*imp)-TS$$

ImP: impact of estimated postponed appointments
Psi: a postponed schedule from patient i
Imp: importance level of this postponed schedule
TS: number of schedules that can be transferred to another medical device.

The relation between the impact of postponed schedules and the cost can be provided by the hospital. In a simple embodiment, a planned treatment has an associated cost that is a fraction of the missed income associated with the treatment plus a penalty due to the increased risk for the patient and the administrative costs of rescheduling patients.

More factors could be taken into account such as an impact on the hospital reputation, impact on the rescheduling of medical personnel.

Tables 1 and 2 (below) can show example results of the likelihood score 132 and the timeframe 134. Table 1 shows an example which indicates a better choice of calling a vendor or maintenance employee to do the service action based on the analysis. Table 2 shows an example which indicates a better choice the bio-med performing the service action themselves.

TABLE 1

|  | Likelihood to be resolved (from 1 to 5) | Cost (1 to 10) for the hospital |
|---|---|---|
| Hospital | 4 | 8 |
| Maintenance | 5 | 1 |

TABLE 2

|  | Likelihood to be resolved (from 1 to 5) | Cost (1 to 10) for the hospital |
|---|---|---|
| Hospital | 5 | 1 |
| Maintenance | 5 | 3 |

FIG. 3 shows an example of the UI 140. As shown in FIG. 3, similar tables like Tables 1 and 2 can be shown, along with a description of the problem with the medical device 120 and a recommendation of the resolution pathway. The UI 140 could be a dashboard item in the current tool a user is using or a dedicated tool. On demand, the user can see the details how these ranks/scores are computed. Optionally, he can adjust the relevant KPI's, then the analysis will compute the result accordingly.

Figure 4:
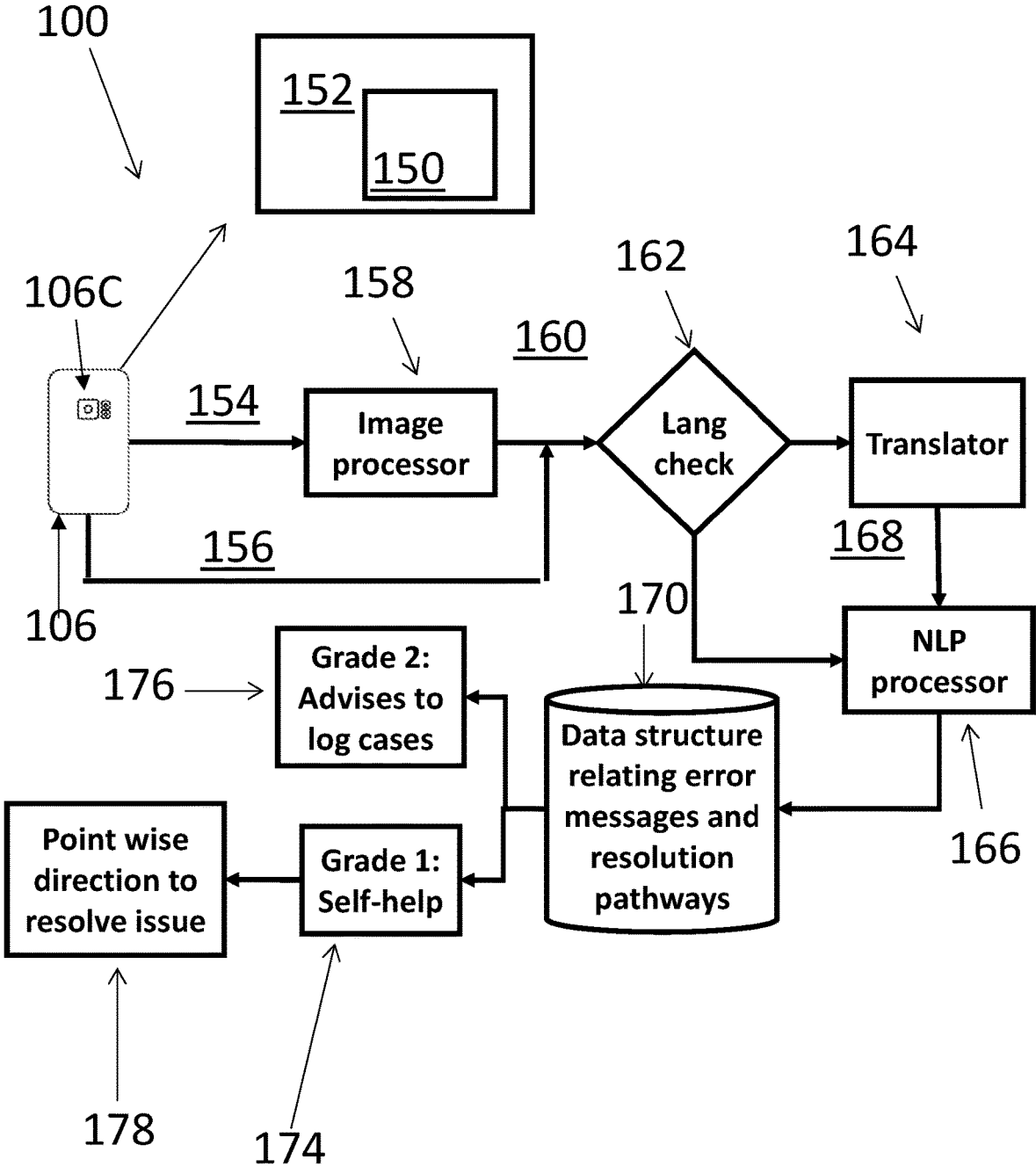
FIG. 4 shows another embodiment of the system of FIG. 1.
Figure 5:
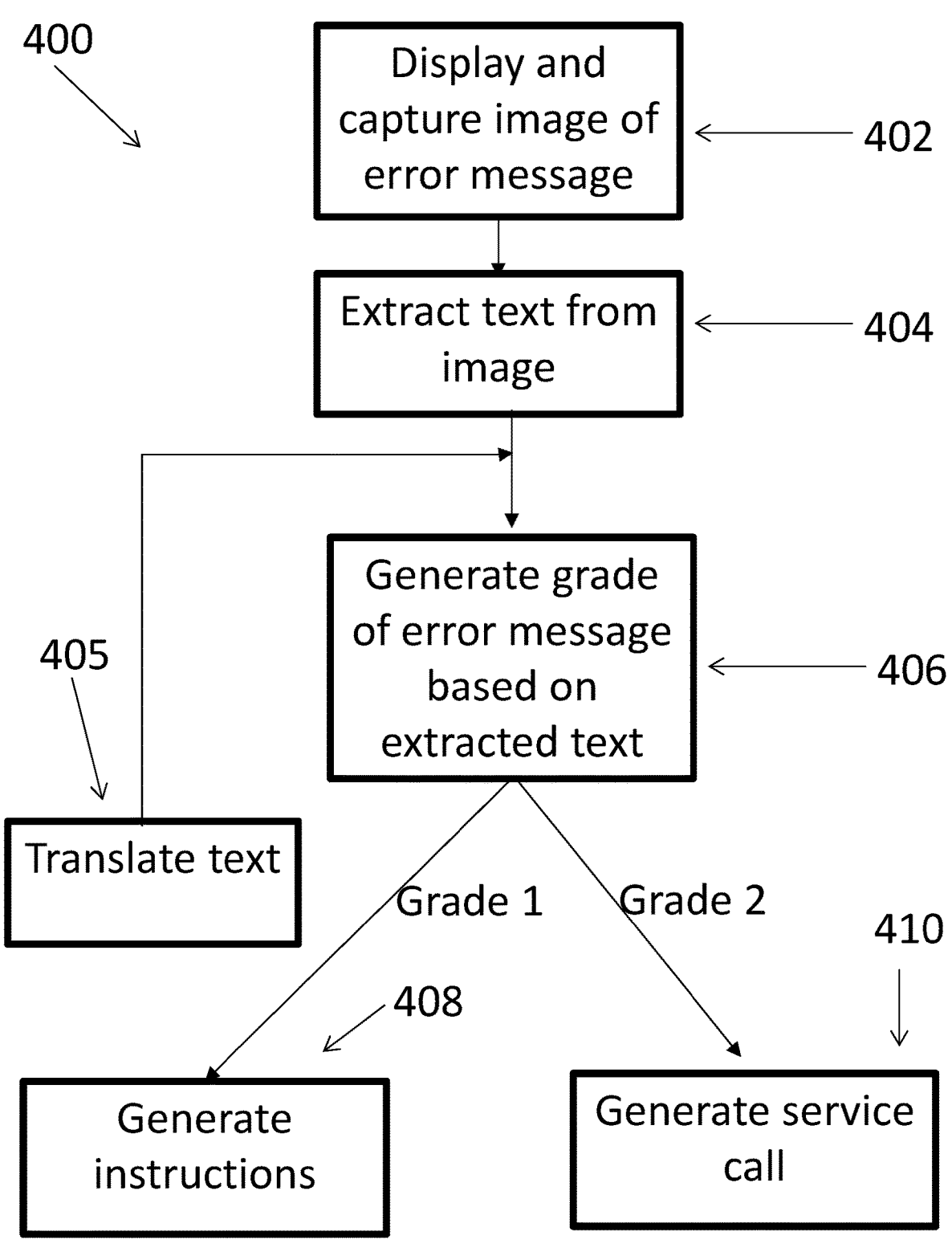
FIG. 5 shows exemplary flow chart operations of the system of FIG. 4.
Figure 6:
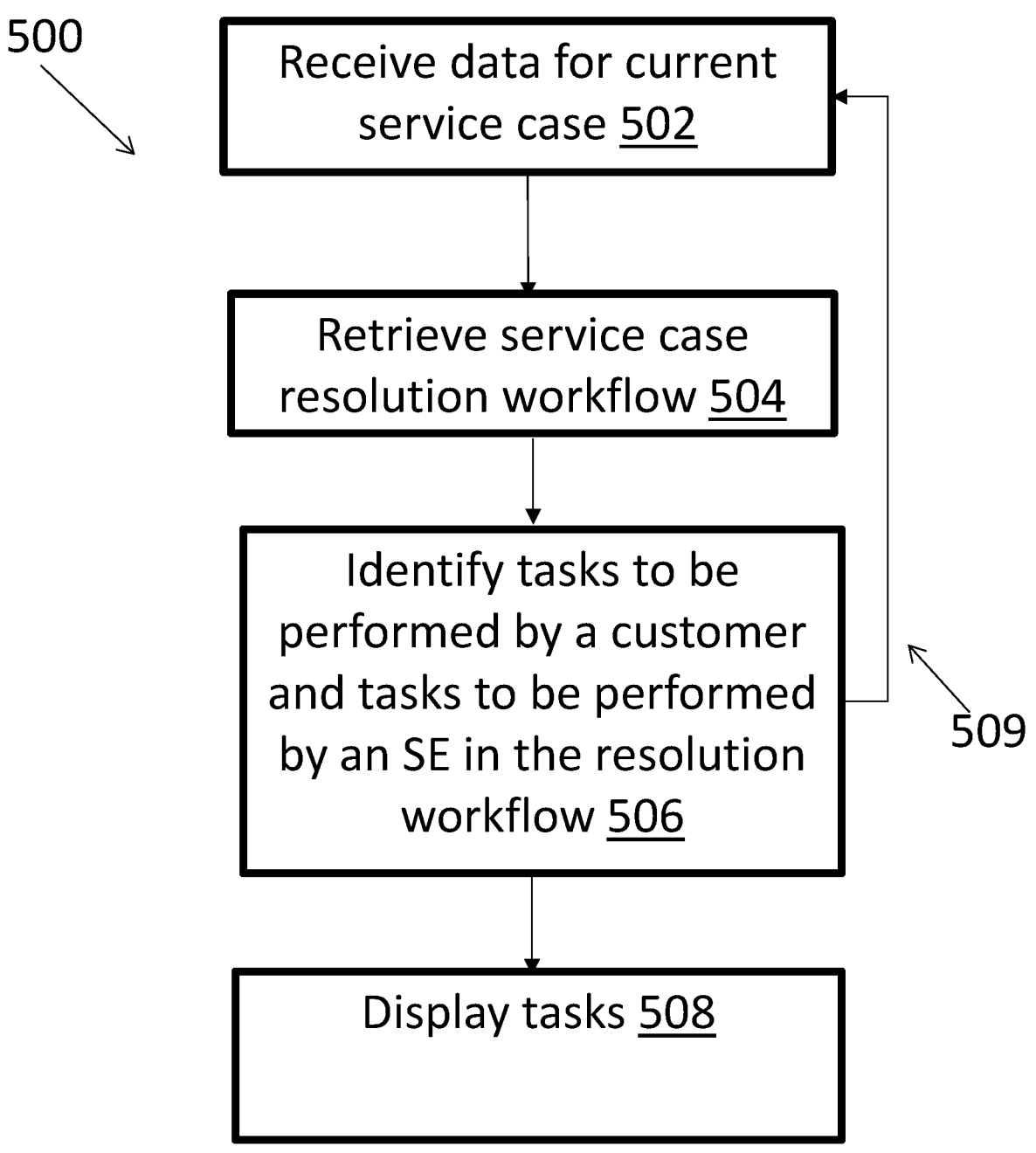
FIG. 6 shows another exemplary flow chart operations of the system of FIG. 1.

With reference now to FIG. 4 and with continuing reference to FIGS. 1-3, FIG. 4 shows another embodiment of the servicing support system 400. In this embodiment, the query for support is received in the form of an image, from a digital camera or an electronic device 106 that includes a digital camera 106C, of an error message displayed by the medical imaging device 120. When some types of issues arise in the medical device 120, an error message 150 is displayed on a display device 152 of the medical device 120. A technician can acquire an image 154 of the error message 150 with the cell phone 106 and transmit the image to the electronic device running the method 200 (or, in some embodiments, the method 200 may run on the cell phone 106 itself). Technicians can also add additional comments 156 regarding the error message while uploading the image 154, for example using a soft keyboard shown on the display of the cellphone 106 to add annotations to the image. Capture of errors as images is advantageous over text input by the technicians as crucial details may be left out by them while writing the error description. Chances of misrepresentation of the error decreases while using images. In this regard, it should be noted that the imaged error message could be complex, for example including various error codes and so forth some of which may include computer software module or component identification numbers or codes or so forth which may not be readily understandable by the technician.

An image processor 158 is configured to extract text 160 from the captured image 154 containing the error message 150. The image processor 158 can be an Optical Character Recognition (OCR) based image processor 158. The image processor 158 analyzes and extracts the useful information from the error image 150. The image processor 158 first eliminates the noise from the image. The image processor 158 further includes a Conventional Neural Network (CNN)-based sliding window that is then passed over the image 154 to detect the text 160. The image may be acquired, for example, using a special application program ("app") running on the cellphone 106 which advises the user to focus and capture only the error message 150 shown on screen and not the background to limit the noise. Additionally or alternatively, the app running on the cellphone 106 may perform automatic cropping of the acquired image to remove the background. (A combination of these may be useful, since excessive cropping can reduce image resolution, so it is advantageous for the user to set the field of view of the image to at least frame the error message well and then use automatic cropping to remove any remaining background).

In some embodiments, the image processor 158 can perform a language detector processor 162 on the extracted text 160. The extracted text 160 from the image 154 along with the additional feedback and comments 156 from the technician are passed to the language detector processor 162. The language detector processor 162 validates whether the extracted text 160 is in, for example, English, or else a mapping process is performed to convert the text to English language. To do so, a natural language toolkit (NLTK) library can be used. If a language of the extracted text 160 is in a different language than a programmed language of the medical device 120, then the extracted text 160 is transmitted to a translator processor 164. If the languages match, then the extracted text 160 is transferred to a natural language processor (i.e., an NLP processor) 166. Translated text 168 from the translator processor 164 can also be transmitted to the NLP processor 166.

Keywords from the extracted text 160 are input to a data structure 170 relating error messages and service case resolution pathways, such as a lookup table or a relational database. The data structure 170 stores error messages, solution, approximate time required to resolve the issue and a grade (Grade 1 174, Grade 2 176). The grade indicates whether the issue can be handled by the technicians employed by a facility at which the medical device 120 is disposed (Grade 1) or if FSE guidance is required from a maintenance technician not employed by the facility (Grade 2). The data structure 170 may comprise a table with columns including an error message column (containing error messages from the previously solved cases), a solution column (point wise directions to resolve the maintenance issue), an approximate time require column (approximate time required to resolve the maintenance issue), a grade column (information on whether the solution can be implemented by the local technician), and so forth.

The data structure 170 utilizes a mapping process to map the data in the columns of the table with keywords in the extracted text 160 to display a point wise solution 178 and the time required for resolution for the Grade 1 errors. If the error is a Grade 2, advice to log a ticket is given. The user can choose the desired language in which the solution will be displayed. If the user exceeds the time indicated in the data structure 170, a pop up is displayed on the GUI 140 asking users if they would like to continue with the diagnostics or if they would like to log an incident requesting FSE guidance or support.

When each case is solved, the extracted text 160 should be saved in the Error Message column of the table. The Solution column is populated based on the actions taken by the SE to resolve the issue in the past. This column can be created by using the case activity data from the other columns in the table. The approximate time required can be calculated from the case activity data. The SE's guidance is initially required to grade the cases based on their complexity. This information will be then utilized to populate the Grade column.

With continuing reference to FIGS. 1-4, FIG. 5 shows another embodiment of the method 400. At an operation 402, an error message 150 is displayed on the display device 152 of the medical device 120 (i.e., the UI 140 can be provided on the display device 152), and an image 154 of the error message 150 is obtained or captured, for example using the camera 106C of the cellphone 106.

At an operation 404, text 160 is extracted from the image 154 with the image processor 158. For example, the extraction operation 404 can be performed using an OCR process. The extracted text 160 includes text related to an issue with the current medical imaging device 120. In some embodiments, a user can provide indicative of additional text 156 to be included in data for the medical imaging device 120 to resolve the error message 150.

In some embodiments, at an optional operation 405, a language of the extracted text 160 (and the additional text 156) can be detected with the language detector processor 162. The language detector processor 162 determines whether the detected language of the extracted text 160 (and/or the additional text 156) matches a language used by the current medical imaging device 120 to resolve the error message 150. If the languages do not match, the translator processor 164 translates the extracted text 160 into the language used by the medical imaging device 120.

At an operation 406, a grade 174, 176 indicative of a pathway to resolve the issue with the current medical imaging device 120 is generated. The generated grade 174, 176 can be included as a component of the resolution likelihood score 132 and the timeframe 134 for resolving the issue with the current medical imaging device 120. To do so, the extracted text 160 is input to the table of the data structure 170. The keywords in the extracted text 160 are mapped to data stored in the table to determine the grade 174, 176.

In one embodiment, the generated grade 174 can be referred to as a "Grade 1" and is indicative of resolving the issue with the current medical imaging device 120 with a facility employee at a facility where the current medical imaging device 120 is disposed (i.e., a bio-med). In this embodiment, the method 400 proceeds to an operation 408, where instructions (i.e., the pointwise solution 178) are generated and displayed on the display device 152 for the bio-med to resolve the issue with the current medical imaging device 120.

In another embodiment, the generated grade 176 can be referred to as a "Grade 2" and is indicative of resolving the issue with the current medical imaging device 120 with a maintenance employee who is not an employee at a facility where the current medical imaging device is disposed (i.e., a SE). In this embodiment, the method 400 proceeds to an operation 410, where a service call for the SE is generated, and the service call is placed to the SE to come to the facility and resolve the issue with the medical device 120.

In some embodiments, a scale of the grades 174, 176 can be binary (i.e., ranging from zero to one). In other embodiments, the grading scale could be more elaborate, e.g., including additional categories (FSE/biomed/wizard, for example) and/or a continuous grading system providing information equivalent to a likelihood of solution. (For example, if a computed continuous grade is 0.9 this may be interpreted as indicating it is very likely the biomed can resolve the problem in-house; whereas a grade of 1.3 might be interpreted as a recommendation to solve the problem in-house by the biomed but with a lower likelihood of success than would be inferred from a score of 0.9.

In another aspect, the solution steps of the workflow are classified as to complexity, and step complexity is compared with a skill level of the customer, and based on this comparison one or more low-complexity steps are identified which can be performed by the customer. These low-complexity steps are assigned to be performed by the customer ahead of the visit from the service engineer. In this way, the work of the SE is simplified by eliminating these low complexity step(s) from the workload of the service engineer.

With continuing reference to FIGS. 1-5, FIG. 6 shows an embodiment of the method 500 which provides for such allocation of low-complexity steps to the customer. At an operation 502, data related to a current medical imaging device 120 for which a current service case to be performed is retrieved based on a query received for the current service case. At an operation 504, at least one service case resolution workflow 180 comprising tasks for the current service case is retrieved from the non-transitory computer readable medium 127.

At an operation 506, (i) a first subset of the tasks of the at least one service case resolution workflow to be performed by a customer of the current medical imaging device, and (ii) a second subset of the tasks of the at least one service case resolution workflow to be performed by a service engineer are identified from the retrieved data and the at least one service case resolution workflow 180. This identifying operation 506 can be performed in a variety of manners.

In some embodiments, the at least one service case resolution workflow 180 is extracted from a service manual 182 stored in the non-transitory computer readable medium 127. The extracting includes identifying an ordered sequence of tasks of each retrieved service case resolution workflow 180. For example, a representation of the at least one service case resolution workflow 180 in the service manual 182 comprises an image of a flowchart, and the extraction of the ordered sequence of tasks of each service case resolution workflow 180 includes (i) identifying tasks of the service case resolution workflow 180 as blocks of the flowchart, (ii) performing OCR on the image of the flowchart to extract text associated with the blocks of the flowchart, and (iii) extracting one or more features of the tasks from the extracted text.

In another example, a representation of the at least one service case resolution workflow 180 in the service manual 182 comprises text, and the extraction of the ordered sequence of tasks of each service case resolution workflow 180 includes (i) performing NLP on the text, and extracting one or more features of the tasks from the NLP operation.

In some embodiments, complexity values can be assigned to the tasks of the at least one service case resolution workflow 180. The identification of the first and second subsets of the tasks of the at least one service case resolution workflow 180 is based at least on the assigned complexity values. To do so, an input indicative of a skill of the customer is received by the server 111, and the identification of the first and second subsets of the tasks of the at least one service case resolution workflow 180 is based at least on the assigned complexity values and the input indicative of the skill of the customer.

In a particular example, at least some tasks of the at least one service case resolution workflow 180 are to be performed in an ordered sequence. In this example, the identification of the first and second subsets of the tasks of the at least one service case resolution workflow 180 is based at least on a criterion that no task of the first subset of the tasks to be performed by the customer is after any task of the second subset of the tasks to be performed by the service engineer in the ordered sequence. Stated another way, a task of the service case resolution 180 cannot be assigned to the customer if the task is dependent on a task that must first be performed by the service engineer. In another example, when at least some tasks of the at least one service case resolution workflow 180 are to be performed in an ordered sequence, the identification of the first and second subsets of the tasks of the at least one service case resolution workflow is based at least on a criterion that one or more tasks of the first subset of the tasks to be performed by the customer is performed after any task of the second subset of the tasks to be performed by the service engineer in the ordered sequence. For example, the customer can perform a first task and a second task in the ordered sequence, the SE performs a third task, the customer performs a fourth task (i.e., downloading new software), and the SE performs a fifth and final task in the ordered sequence (i.e., restarting a system with the new software).

In some cases, a task for the SE to check the solution steps performed by the customer can be added to the second set of tasks. For example, a customer can learn how to perform specific tasks by watching the SE perform them during a service call. The system 100 can then receive inputs from the customer indicative of the customer knowing how to do the now-learned tasks. In this manner, a knowledge of the customer can be updated in the system 100 based on results of the SE checking the solution steps performed by the customer (indicated with a feedback arrows 509 in FIG. 6).

At an operation 508, the GUI 140 is provided to show (i) the identified first subset of the tasks of the at least one service case resolution workflow to be performed by the customer and (ii) the identified second subset of the tasks of the at least one service case resolution workflow to be performed by the service engineer. The GUI 140 may be presented on the service device 102 of the service engineer, as shown in FIG. 1. The operation 508 may also optionally present at least the first subset of the tasks to the customer via a suitable pathway. For example, the operation 508 may construct and automatically send an electronic mail (email) or other electronic message to the customer instructing the customer to perform the tasks of the first subset of tasks before the service engineer visits. Alternatively, this communication may be done manually by the service engineer after receiving the identification of the first and second subsets of tasks via the operation 508. Optionally, an incentive and/or compensation may be provided to the customer for performing the first subset of tasks, such as a reduction in the cost of the service call. (Typically, at a minimum the customer benefits by not being charged for the labor of the service engineer with respect to those tasks that are performed by the customer.)

The following describes embodiments of the system 100 and the method 500 in more detail. In the method 500, the system 100 is configured to analyze and extract features from the solution steps of a problem using NLP techniques, triage or classify the steps for that particular solution (e.g., easy, complex, sensitive, time consuming, independent, immediate, etc.), and assess which steps can be performed by user and assist the user to perform that step. The role of the user, if available, can also be considered for the assessment.

Every time the service engineer visits and some of these non-critical steps can be done along with the user/biomed to make them acquainted so that it can be done by them for repeat occurrence. The system 100 can then update the database, retrain the algorithm periodically to determine steps which can be done by the user. This way personalization can be done per user while determining which step can be done by the user. When the FSE visits, these steps are already completed and the FSE can concentrate on the more critical steps of the solution. When more than one solution can be applied to a certain problem, the system 100 can provide steps that are equal between the two solutions and that can be applied by the user until a point where the two solutions proceed differently and a FSE has to make a decision how to proceed.

Figure 7A:
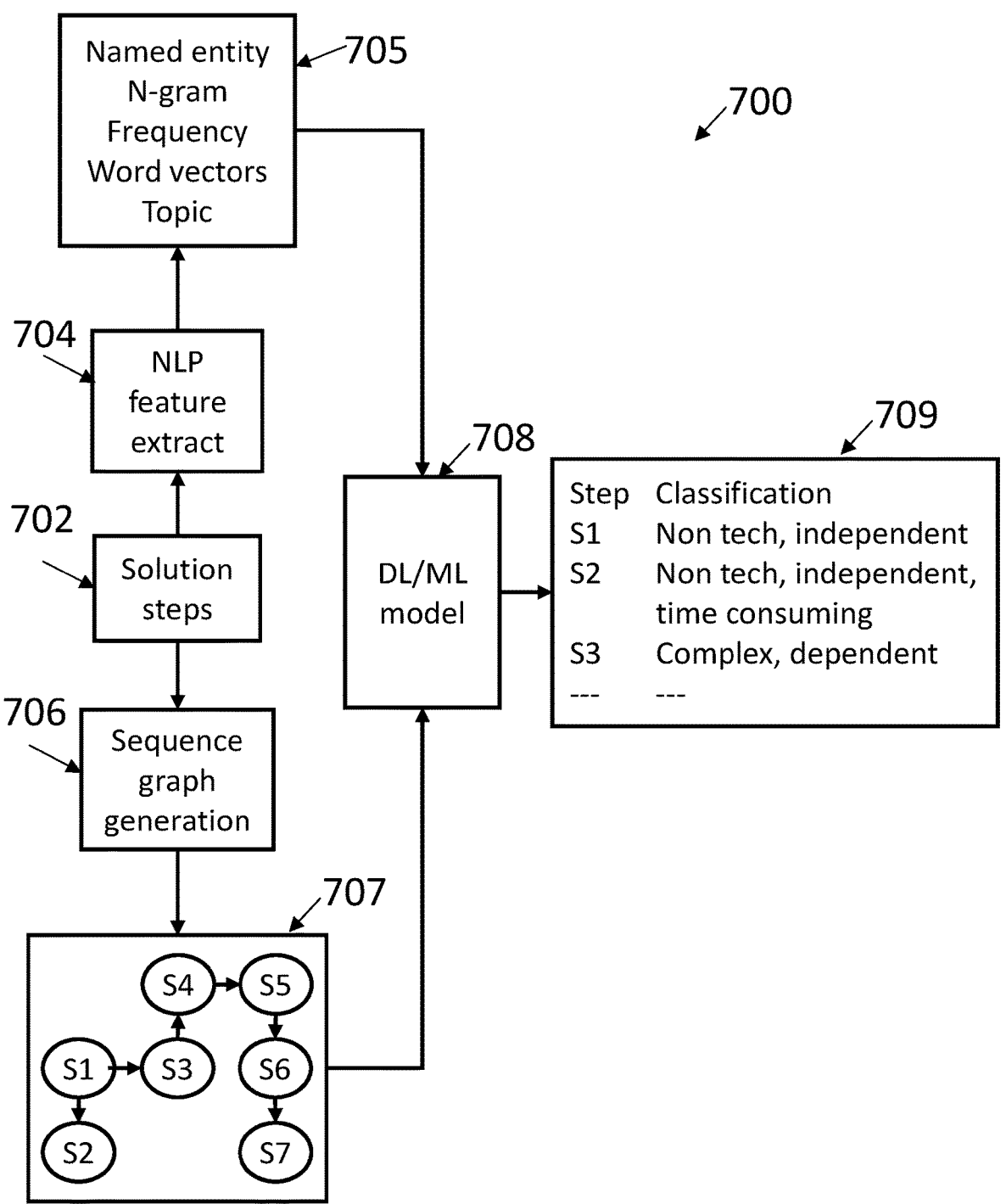
FIGS. 7A and 7B show offline and online phases, respectively, of an embodiment of the operations of FIG. 6.
Figure 7B:
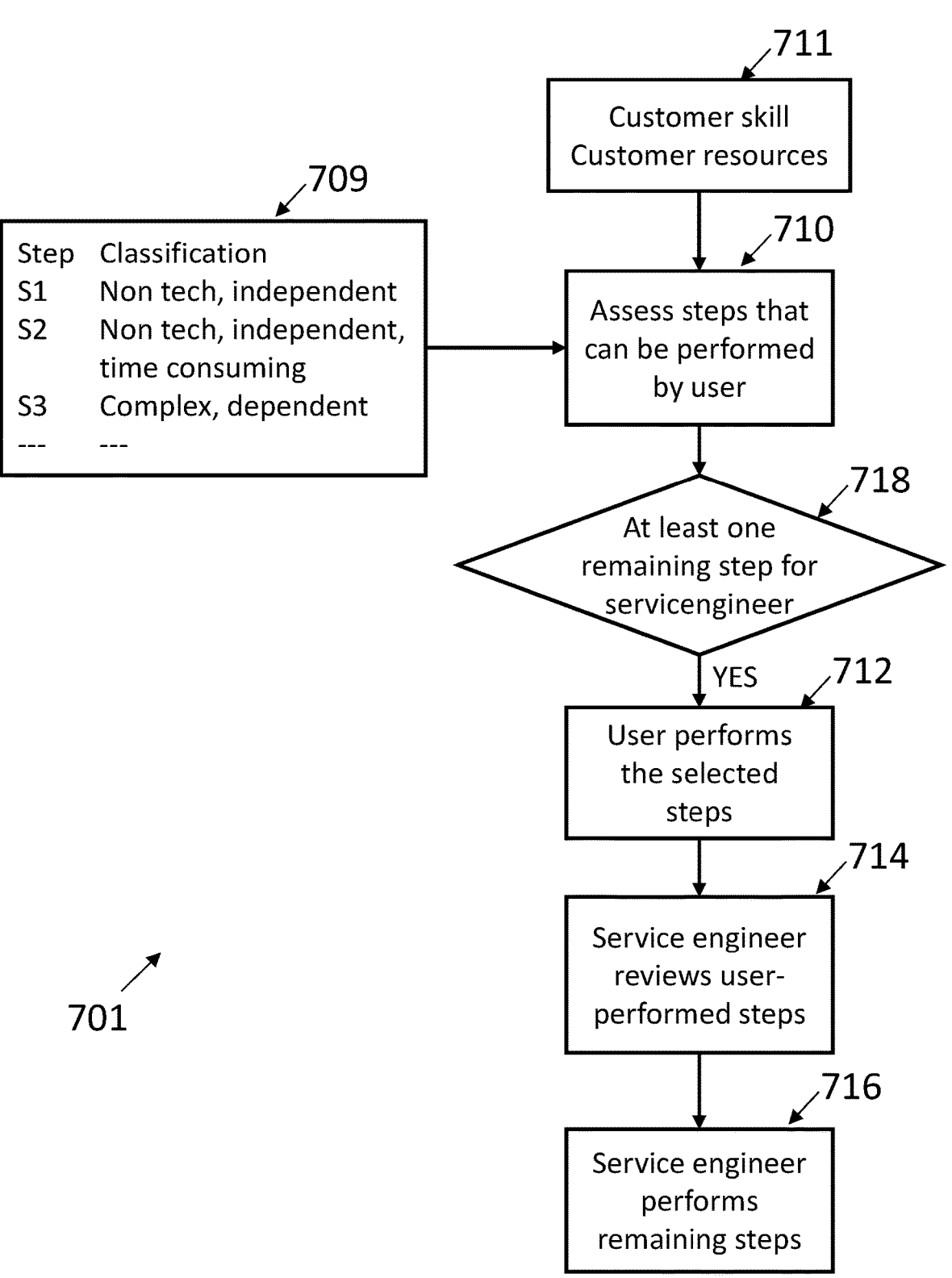

The triaging process is shown in FIGS. 7A and 7B as a flowchart of operations 700 (FIG. 7A) and 701 (FIG. 7B). Referring first to FIG. 7A, at an operation 702, a solution for a reported issue is identified in the service manual 182, and text describing the solution is extracted from the service manual 182. The extracted solution text is pre-processed to extract the features and sequence of steps that provides more insights of the text. To do so, at an operation 704, a solution text is pre-processed and analyzed through a set of NLP techniques to extract relevant features such as named entity, N-gram, word vectors, topic etc. (shown with reference character 705). At an operation 706, a sequence graph is generated by processing the solution text. This sequence graph contains the different steps of the solution, resulting in a sequence graph of performing each step and the interdependency among the steps (shown with reference character 707). The ordering of steps can be derived in various ways. If the text lists steps in a sequence, this sequence can be used. Branching textual cues such as "if $<$ . . . $>$ then $<$ . . . $>$" can be detected to identify branches in the sequence graph. If the solution steps input 702 already includes a graphical representation, e.g. the solution text being extracted from boxes of a resolution flowchart, then that graphical representation can be used to form the sequence graph 707. It is also noted that one or both of the operations 704 and 706 could optionally be done manually, i.e. the keywords and/or other features 705 and/or the steps sequence graph 707 could be manually constructed.

At an operation 708, after extracting the features 705 and generation of the sequence graph 707, a deep learning and/or machine learning (DL/ML) model is trained using these features 705 and sequence graph 707 to classify the steps in different classes such as easy, complex, sensitive, time consuming, independent, immediate etc. (shown with reference character 709). A step can be assigned to multi-class by this classification model. The DL/ML model 708 may, for example, be an artificial neural network (ANN), support vector machine (SVM), or other DL or ML model that is suitably pre-trained on test solution step sequences manually annotated with complexity values to classify steps as to complexity. In general, the training of the DL/ML model 708 may associate certain terms, N-grams, word vectors, topics, and combinations thereof with different complexity levels. For example, if the test sequences usually label steps that involve opening the housing of a certain component as highly complex, then the training operates to train the DL/ML model 708 to label steps that include terms, N-grams, or so forth corresponding to opening the housing of that component as highly complex. Conversely, if the test sequences usually label steps that involve imaging a phantom as non-technical (low complexity), then the training operates to train the DL/ML model 708 to label steps that include terms, N-grams, or so forth corresponding to imaging the phantom as low complexity. These are merely nonlimiting illustrative examples.

The output of the operations 700 of FIG. 7A for a given input set of solution steps 702 is the sequence of complexity-classified steps 709. In some implementations, the process 700 is applied in an offline fashion to various resolution pathways, with each resolution pathway represented by corresponding text of solution steps 702. For example, the process 700 could be applied to each resolution pathway contained in a service manual for a particular medical imaging device (or class of such devices). This can be done since the complexity of steps of a given resolution pathway is dependent only on the text of solution steps 702, and not on the circumstances of any particular service case. Hence, running the process 700 of FIG. 7A on many or all of the various resolution pathways in such an offline fashion beneficially provides the corresponding respective sequences of complexity-classified steps 709 which are then available for use in assigning low complexity tasks to the customer in a given current service case.

However, whether the customer in a given current service case can actually perform a given step that is classified as low complexity may depend on factors such as the skill level of the customer and the resources available to the customer. For example, if the customer is a large hospital with on-staff personnel with training in maintaining imaging devices then the customer may be considered to have a high skill level and is readily able to perform low complexity tasks. On the other hand, if the customer is a small hospital or clinic with no on-staff maintenance personnel at that level of training, then such a customer may only be able to perform very low complexity steps such as performing imaging of a phantom. Additionally, the ability of the customer to perform a low complexity task may depend on the resources available to the customer. In the last example, the customer can only perform the phantom imaging step if the customer has the appropriate imaging phantom on-hand at the hospital. Similarly, some steps may require specialized instruments and can only be performed by a customer with such instruments on-hand. Hence, the sequence of complexity-classified steps 709 output by the process 700 of FIG. 7A is not, by itself, sufficient to assign a subset of tasks to be performed by the customer.

Rather, with reference now to FIG. 7B, in a process 701 for a given current service case triaging 710 of the steps is performed based on the complexity classes the steps as represented by the sequence of complexity-classified steps 709 and also based on data 711 related to the current medical imaging device for which the current service case to be performed. At the operation 710, the steps that can be performed by user are assessed based on the triage score with respect to combination of certain assigned classes such as non-technical, time consuming, independent, and so forth. A semi supervised way to assigning these classes is by looking at the steps. For example, if the steps involved opening the cabinet and further unscrew certain components, it needs certain specific skills and prior knowledge. Such tasks are labelled as technical and complex by the process 700 of FIG. 7A. Only if the information 711 indicates the customer has the skill and resources to perform such a complex step can the operation 710 assign that task to the customer. However, a step involving only restarting the system and noting down certain parameters, does not need any specific skill and is thus labelled as easy and non-technical by the process 700 of FIG. 7A, and hence the operation 710 assigns that task to the customer. The sequence of the complexity-classified steps 709 also may factor into whether the operation 710 assigns a given step to the customer. For example, even if a step is of low complexity and can be performed by the customer based on the skill/resources 711 of the customer, if that step depends on an earlier step that cannot be performed by the customer than it cannot be assigned to the customer. The sequence graph 707 has the steps identified and from previous service actions, time taken can be considered if its time consuming. The database of sequences of the complexity-classified steps 709 for various resolution pathways that has been built offline using the process 700 of FIG. 7A serves as an input 709 to the online process (i.e., per-service case process) 701 of FIG. 7B. In an operation 712, the user (i.e. customer) performs the first subset of the steps which were assigned to the customer in the operation 710. The role (e.g. skill level and resources 711) of the user, if available, can also be considered for the assessment.

Safety aspects may also be examined for each of the steps that have been assigned to the user. Specifically after the last user assigned step there preferably is at least one operation which is carried out by the RSE/FSE, indicated as the operation 714. This enables the RSE/FSE to check that the previous steps performed by the customer have been carried out within the normal maintenance protocol and have resulted in a status of the machine which is still safe for both further maintenance and for final release for customer usage. As a consequence, the last step is assigned to the RSE/FSE as an operation 716 even if it is identified as candidate which can assigned to the user. This is indicated as an operation 718. In this modified workflow, when the FSE visits certain steps have already been performed by the user, and the FSE can concentrate on the more critical steps of the solution.

Figure 8:
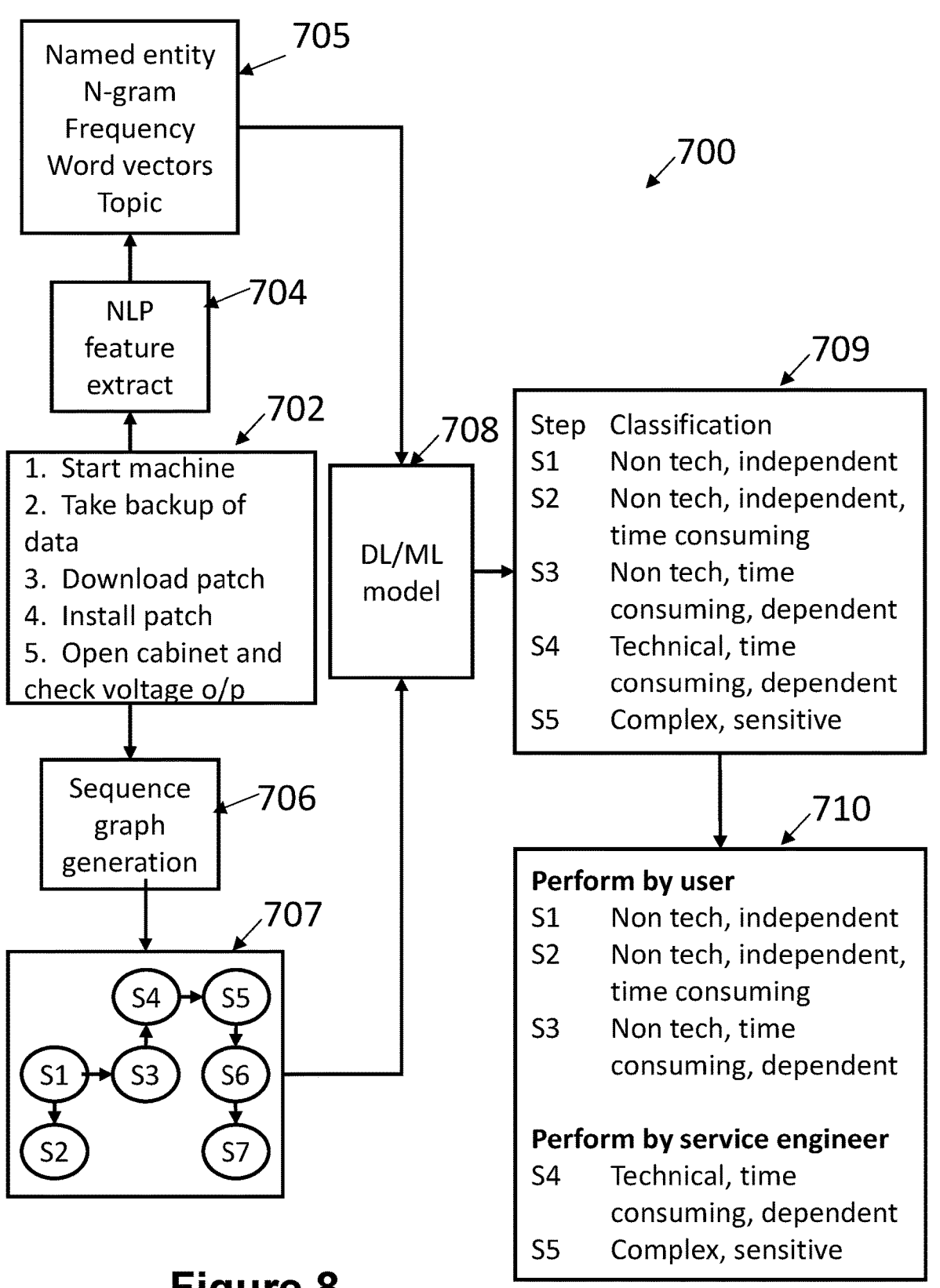
FIGS. 8-10 show further embodiments of the operations of FIG. 6.

FIG. 8 shows a flowchart of an example of the process 700 of FIG. 7A for a use case where FSE has to update the software in a medical system as a solution to a reported problem. The operation 702, 704, 706, and 708 are first performed. In the operation 708, the AI model is used to classify each step to different combination of classes (depicted at 709) and then at the operation 710, these steps are assessed as to which steps can be performed by the user, in this example steps S1, S2, and S3 are assigned to user, and the rest of the steps (i.e. steps S4 and S5) are assigned to be performed by the FSE.

Figure 9:
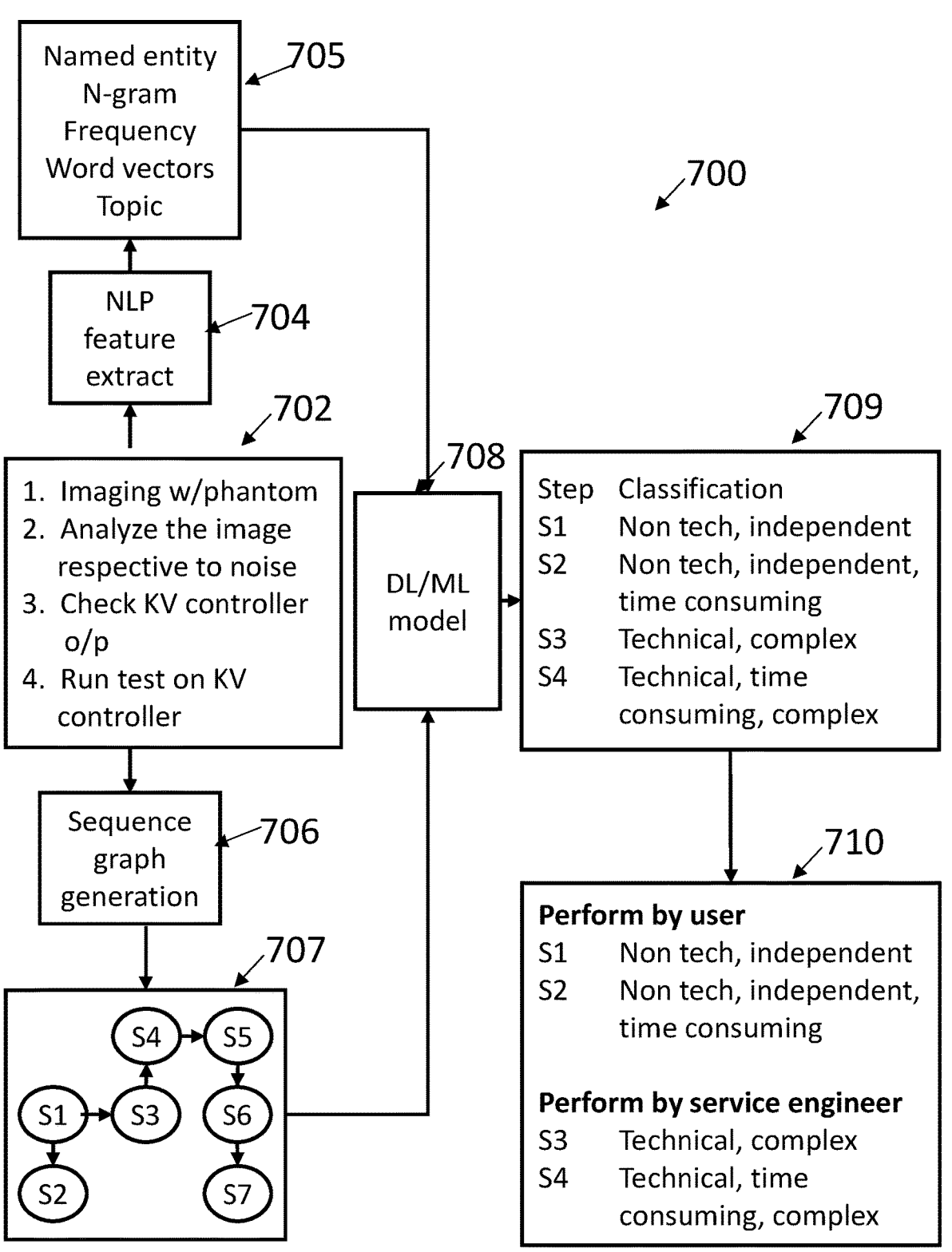

FIG. 9 depicts another use case where noise in the image is reported by the user as an issue and how our proposed methodology triage/classify the steps that can be performed by the user. Here steps S1, and S2 is selected to be performed by the user, and the rest of the steps (i.e. steps S3 and S4) are assigned to be performed by the FSE.

Figure 10:
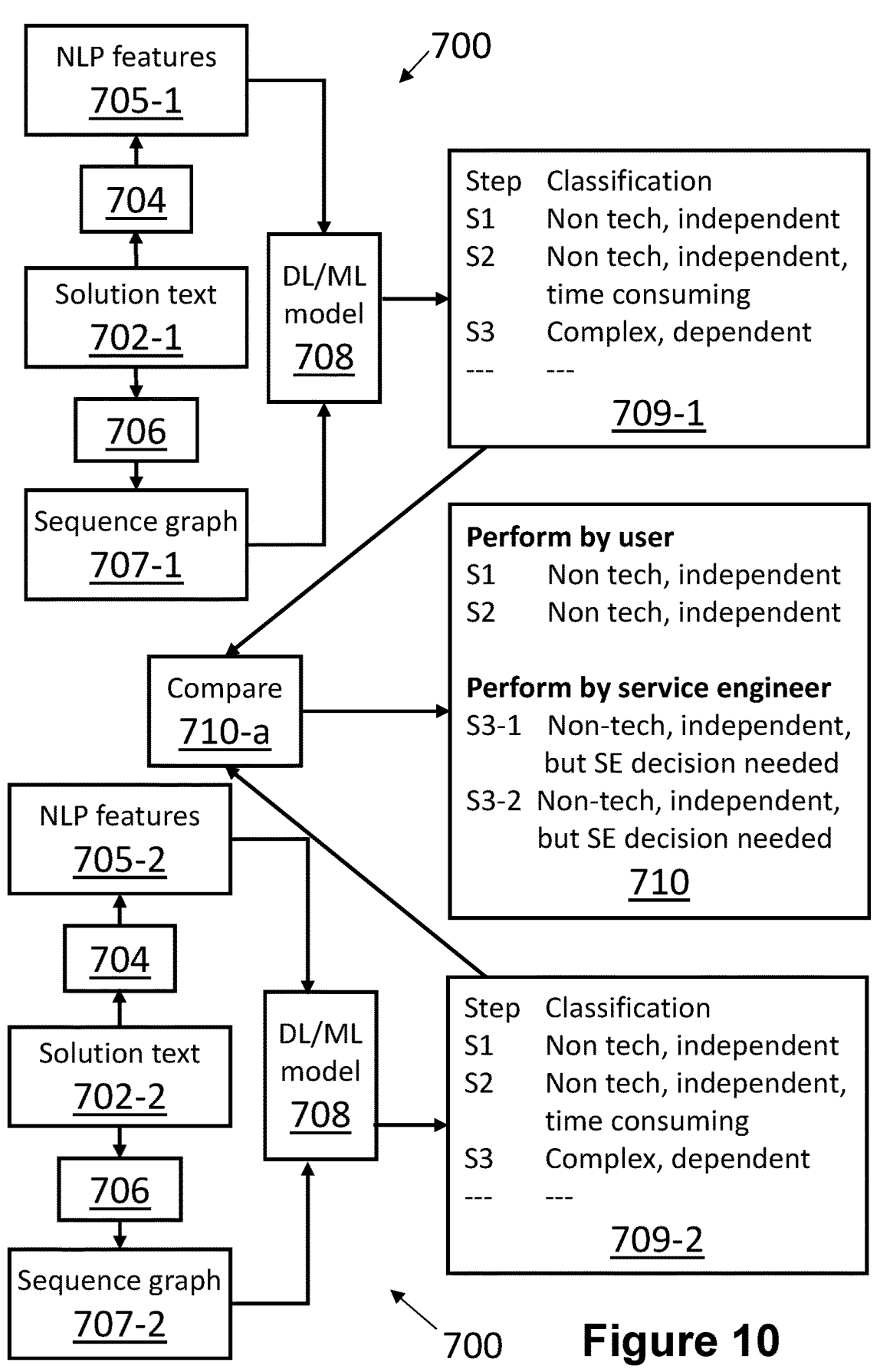

FIG. 10 depicts another use case where more than one solution may apply to the issue with the medical device 120. In FIG. 10, one solution is denoted as solution text 702-1 and another (different) solution is denoted as solution text 702-2. For the solution text 702-1, the operations 704 and 706 of the offline process 700 produce NLP features 705-1 and sequence graph 707-1, respectively, which are input to the DL/ML model 708 to produce the sequence of complexity-classified steps 709-1 corresponding to the solution text 702-1. For the solution text 702-2, the operations 704 and 706 of the offline process 700 produce NLP features 705-2 and sequence graph 707-2, respectively, which are input to the DL/ML model 708 to produce the sequence of complexity-classified steps 709-2 corresponding to the solution text

702-2. Here, the combination of classes depicted at 709-1 and 709-2 can be compared at an operation 710-a, and then at the operation 710, these steps are assessed as to which steps can be performed by the user, in this example step S1 and S2 can be assigned to user and step S3-1 (from solution text 702-1) and S3-2 (from solution text 702-2) can include a decision by the FSE as to how to proceed.

A non-transitory storage medium includes any medium for storing or transmitting information in a form readable by a machine (e.g., a computer). For instance, a machine-readable medium includes read only memory ("ROM"), solid state drive (SSD), flash memory, or other electronic storage medium; a hard disk drive, RAID array, or other magnetic disk storage media; an optical disk or other optical storage media; or so forth.

The methods illustrated throughout the specification, may be implemented as instructions stored on a non-transitory storage medium and read and executed by a computer or other electronic processor.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A non-transitory computer readable medium, storing:

data related to medical imaging devices; and instructions readable and executable by at least one electronic processor to:

retrieve, based on a query received for the current service case, data related to a current medical imaging device for which the current service case to be performed;

generate, from the retrieved data and for each of a plurality of available service case resolution pathways by applying predefined rules or executing a trained machine learning model using inputs derived from the retrieved data including complexity analysis (C) from technical documents, number of escalated cases (E), and reoccurrence (R) of the problem on the current medical imaging device, (i) a resolution likelihood score indicative of a likelihood of the resolution pathway resolving the current service case, and, using inputs including the complexity analysis (C) and repair time of historical service records (R) for the same medical device type, and (ii) a timeframe for the resolution pathway to resolve the current service case; and provide, on a display device of an electronic processing device, a user interface (UI) the generated resolution likelihood score and the generated timeframe for the resolution pathways.

2. The non-transitory computer readable medium of claim 1, further comprising:

receiving the query including receiving, from a digital camera or an electronic device that includes a digital camera, an image of an error message displayed by the current medical imaging device;

wherein the retrieving of the data related to the current medical imaging device includes performing optical character recognition (OCR) to extract the error message from the image.

3. The non-transitory computer readable medium of claim 2, wherein the instructions further include:

detecting a natural language of the error message;

determining whether the detected language of the extracted text matches a language used by the current medical imaging device; and translating the detected language into the language used by the current medical imaging device if the detected language does not match the language used by the current medical imaging device.

4. The non-transitory computer readable medium of claim 1, wherein the generating the resolution likelihood score includes:

generating the resolution likelihood score as a grade indicative of a pathway to resolve the issue with the current medical imaging device.

5. The non-transitory computer readable medium of claim 1, wherein the resolution pathway comprises a customer employee of the customer of the current medical image device, and the generation, from the retrieved data, of (i) a resolution likelihood score indicative of a likelihood of the customer employee resolving the current service case, and (ii) a timeframe for the customer employee to resolve the current service case further includes:

generating the resolution likelihood score indicative of the likelihood of the customer employee resolving the current service case based on a historical effectiveness of the customer employee in resolving historical service cases within a predetermined timeframe.

6. The non-transitory computer readable medium of claim 1, wherein the resolution pathway comprises a customer employee of the customer of the current medical image device, and the generation, from the retrieved data, of (i) a resolution likelihood score indicative of a likelihood of the customer employee resolving the current service case, and (ii) a timeframe for the customer employee to resolve the current service case further includes:

generating the resolution likelihood score indicative of the likelihood of the customer employee resolving the current service case based at least on a metric indicative of likelihood that resolution of the current service case includes performing a non-customer-serviceable part replacement.

7. The non-transitory computer readable medium of claim 1, wherein the resolution pathway comprises a maintenance provider employee, and the generation, from the retrieved data, of (i) a resolution likelihood score indicative of a likelihood of the maintenance provider employee resolving the current service case, and (ii) a timeframe for the maintenance provider employee to resolve the current service case further includes:

generating the resolution likelihood score based on a historical effectiveness of the maintenance provider employee in resolving historical service cases within a predetermined timeframe.

8. The non-transitory computer readable medium of claim 1, wherein the instructions further include:

generating the resolution likelihood score and the timeframe for a resolution pathway comprising a customer employee of the customer of the current medical image device;

generating the resolution likelihood score and the timeframe for a resolution pathway comprising a maintenance provider employee; and generating a service call to the customer employee or the maintenance provider based on a higher resolution likelihood score within the timeframe.

9. The non-transitory computer readable medium of claim 1, wherein the instructions further include:

applying a predetermined cost metric to the generated resolution likelihood score and the generated timeframe to determine a cost of resolution for the current service case; and providing the cost of resolution on the display device.

10. The non-transitory computer readable medium of claim 9, wherein determining a cost of resolution for the current service case further includes:

determining a cost of a service call for the current service case and/or costs related to scheduling data related to the current medical imaging device.

11. A servicing support system, comprising:

a database storing data related to medical imaging devices; and at least one electronic processor programmed to:

retrieve, based on a query received for a current service case, data related to a current medical imaging device for which the current service case to be performed;

generate, from the retrieved data and for each of a plurality of available service case resolution pathways by applying predefined rules or executing a trained machine learning model using inputs derived from the retrieved data including complexity analysis (C) from technical documents, number of escalated cases (E), and reoccurrence (R) of the problem on the current medical imaging device, (i) a resolution likelihood score indicative of a likelihood of the resolution pathway resolving the current service case, and, using inputs including the complexity analysis (C) and repair time of historical service records (R) for the same medical device type (ii) a timeframe for the resolution pathway to resolve the current service case, and (iii) a cost of resolution for the current service case; and provide, on a display device of an electronic processing device, a user interface (UI) displaying the generated resolution likelihood score, the generated timeframe for the resolution pathways, and then cost of resolution.

12. The servicing support system of claim 11, wherein the resolution pathway comprises a customer employee of the customer of the current medical image device, and generate, from the retrieved data, (i) a resolution likelihood score indicative of a likelihood of the customer employee resolving the current service case, and (ii) a timeframe for the customer employee to resolve the current service case further includes:

generating the resolution likelihood score based on a historical effectiveness of the customer employee in resolving historical service cases within a predetermined timeframe.

* * * * *